(12) United States Patent
Hseu

(10) Patent No.: US 9,486,148 B2
(45) Date of Patent: Nov. 8, 2016

(54) METHOD AND APPARATUS FOR ESTIMATING DEPTH OF ANETHESIA BY USING ECG SIGNAL

(71) Applicant: Shu-Shya Hseu, Taipei (TW)

(72) Inventor: Shu-Shya Hseu, Taipei (TW)

(*) Notice: Subject to any disclaimer, the term of this patent is extended or adjusted under 35 U.S.C. 154(b) by 251 days.

(21) Appl. No.: 14/288,881

(22) Filed: May 28, 2014

(65) Prior Publication Data

US 2015/0208926 A1   Jul. 30, 2015

(30) Foreign Application Priority Data

Jan. 28, 2014 (TW) .............................. 103103293 A

(51) Int. Cl.
  *A61B 5/04* (2006.01)
  *A61B 5/0205* (2006.01)
  *A61B 5/0402* (2006.01)
  *A61B 5/0452* (2006.01)
  *A61B 5/00* (2006.01)
  *A61B 5/024* (2006.01)

(52) U.S. Cl.
  CPC ........... *A61B 5/0205* (2013.01); *A61B 5/0402* (2013.01); *A61B 5/0452* (2013.01); *A61B 5/4821* (2013.01); *A61B 5/02405* (2013.01)

(58) Field of Classification Search
  CPC . A61B 5/0402; A61B 5/0205; A61B 5/0452

USPC ......................................................... 600/513
See application file for complete search history.

(56) References Cited

U.S. PATENT DOCUMENTS 5,372,140 A * 12/1994 Pomfrett .............. A61B 5/0205
                                                                  600/484

FOREIGN PATENT DOCUMENTS

| CN | 1736324 A | 2/2006 |
|---|---|---|
| TW | 200616639 A | 6/2006 |
| TW | M451978 U | 5/2013 |

OTHER PUBLICATIONS

Yu-Ting Lin, Hau-Tieng Wu, Jenho Tsao, Huey-Wen Yien, Shu-Shya Hseu, Time-varying spectral analysis revealing differential effects of sevoflurane anesthesia: non-rhythmic to rhythmic ratio, Acta Anaesthesiologica Scandinavica, Jan. 10, 2014, pp. 157-167, vol. 58, Issue 2.

* cited by examiner

*Primary Examiner* — Amanda Patton
*Assistant Examiner* — Philip C Edwards
(74) *Attorney, Agent, or Firm* — Hauptman Ham, LLP

(57) ABSTRACT

A method and apparatus for estimating depth of anesthesia includes steps of acquiring an ECG signal from a subject, quantifying the regularity of respiratory sinus arrhythmia (RSA) from the ECG signal to obtain an index, and estimating depth of anesthesia based on the index.

14 Claims, 17 Drawing Sheets

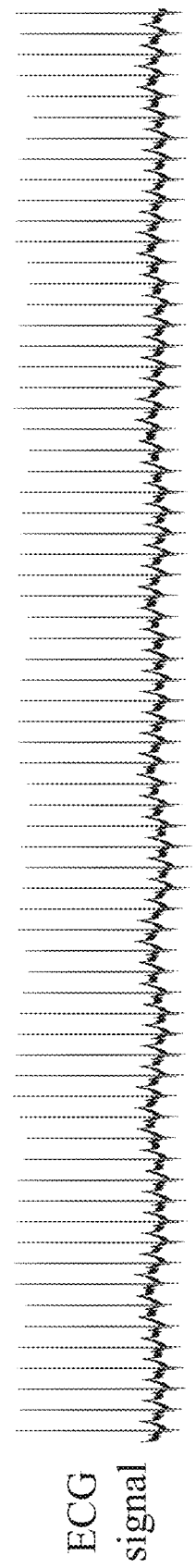

METHOD AND APPARATUS FOR ESTIMATING DEPTH OF ANETHESIA BY USING ECG SIGNAL

CROSS REFERENCE TO RELATED APPLICATIONS

This application claims a priority from Taiwan Patent Application No. 103103293 filed on Jan. 28, 2014. This invention is partly disclosed in a thesis entitled "Time-varying spectral analysis revealing differential effects of sevoflurane anesthesia: non-rhythmic to rhythmic ratio" on Jan. 10, 2014 completed by Yu-Ting Lin, Hau-tieng Wu, Jenho Tsao, Huey-Wen Yien and Shu-Shya Hseu.

FIELD OF THE INVENTION

The present invention relates to a method and apparatus for estimating depth of anesthesia, in particular by quantifying the regularity of respiratory sinus arrhythmia (RSA) based on ECG signals.

BACKGROUND OF THE INVENTION

The methods and apparatuses currently used for estimating depth of anesthesia do so mainly by measuring the activity of the cerebral cortex based on EEG (electroencephalography, EEG). For example, Bispectral Index Monitors® (Covidien company) estimate depth of anesthesia by assessing spontaneous activities of the cerebral cortex based on EEG. However, units of EEG signals are microvolts ($\mu V$), much lower than electrocardiographic (ECG) signal strength, whose units are millivolt (mV). As a result, detecting EEG signals requires very sophisticated apparatuses, which are usually large, heavy, and are expensive and inconvenient to move or to carry. The costs of special electrodes used in these apparatuses are also high. Therefore, the use of EEG as a method for estimating depth of anesthesia is not economical or efficient. Moreover, anesthetics have different effects on different cerebral regions. Typically, only cortical activities are measured based on EEG signals to determine depth of anesthesia, and other important anesthetic factors may not be evaluated effectively, including motor suppression, analgesic and autonomic activities, which are largely controlled by subcortical regions of the brain. Hence, anesthetic conditions of subjects may not be monitored by only using the methods and apparatuses based on EEG.

SUMMARY OF THE INVENTION

A primary object of the present invention is to provide a method and apparatus for estimating depth of anesthesia based on ECG signals, rather than EEG signals, so that this apparatus has a small size, a light or portable weight, and an inexpensive cost without the use of special electrodes, significantly reducing the cost for estimating depth of anesthesia. Furthermore, since the method and apparatus of the present invention mainly measures the activities of the subcortical regions of the brain, instead of measuring the activities of the cerebral cortex, if the method or apparatus is used in combination with other methods or apparatuses for estimating depth of anesthesia based on EEG signals, the anesthetic condition of subjects can be more thoroughly monitored.

To achieve the above object, the present invention provides a method for estimating depth of anesthesia, comprising steps of (a) acquiring an ECG signal; (b) quantifying the regularity of respiratory sinus arrhythmia (RSA) to obtain an index based on the ECG signal; and (c) estimating depth of anesthesia based on the index.

In an embodiment of the present invention, the index obtained from quantifying the regularity is a ratio of a respiratory non-rhythmic component to a respiratory rhythmic component (NRR), the respiratory rhythmic component is a value representing extent of heart rate variability (HRV) affected by respiration, and the respiratory non-rhythmic component is a value representing extent of heart rate variability (HRV) not affected by respiration.

In an embodiment of the present invention, the respiratory rhythmic component is the sum of RRI (R-R intervals) power in a specific bandwidth where a fundamental rhythmic frequency is located and RRI (R-R intervals) power in a specific bandwidth where a multiple of the fundamental rhythmic frequency is located in a specific frequency range in a frequency to power spectrum of RRI, and the fundamental rhythmic frequency is a frequency of a maximal power in a specific frequency range in a frequency to power spectrum of EDR (ECG-derived respiration).

In an embodiment of the present invention, the respiratory non-rhythmic component is total RRI power in a specific frequency range in the frequency to power spectrum of RRI minus the respiratory rhythmic component.

In an embodiment of the present invention, the frequency to power spectrum of RRI and the frequency to power spectrum of EDR are an MTFR (multitaper time-frequency reassignment) spectrum of RRI and an MTFR spectrum of EDR respectively, and the respiratory non-rhythmic component, the respiratory rhythmic component, the fundamental rhythmic frequency, the multiple of the fundamental rhythmic frequency, the RRI power in a specific bandwidth where the fundamental rhythmic frequency is located, or the RRI power in a specific bandwidth where the multiple of the fundamental rhythmic frequency is located is derived from the MTFR spectrum of RRI and the MTFR spectrum of EDR.

The present invention provides an apparatus for estimating depth of anesthesia, comprising an ECG signal acquiring unit acquiring an ECG signal in a non-invasive way, and outputting a digitized ECG signal, and an ECG signal analysis unit coupled with the ECG signal acquiring unit for receiving the digitized ECG signal, and quantifying regularity of respiratory sinus arrhythmia (RSA) to obtain an index based on the ECG signal for estimating depth of anesthesia.

In an embodiment of the present invention, the index obtained from quantifying the regularity is a ratio of a respiratory rhythmic component to a respiratory rhythmic component (NRR), the non-rhythmic component is a value representing the extent of HRV affected by respiration, and the non-rhythmic component is a value representing the extent of HRV not affected by respiration.

In an embodiment of the present invention, the respiratory rhythmic component is the sum of RRI (R-R intervals) power in a specific bandwidth where a fundamental rhythmic frequency is located and RRI (R-R intervals) power in a specific bandwidth where a multiple of the fundamental rhythmic frequency is located in a specific frequency range in a frequency to power spectrum of RRI, and the fundamental rhythmic frequency is a frequency of a maximal power in a specific frequency range in a frequency to power spectrum of EDR (ECG-derived respiration).

In an embodiment of the present invention, the respiratory non-rhythmic component is total RRI power in a specific frequency range in the frequency to power spectrum of RRI minus the respiratory rhythmic component.

In an embodiment of the present invention, the frequency to power spectrum of RRI and the frequency to power spectrum of EDR are an MTFR (multitaper time-frequency re-assignment) spectrum of RRI and a MTFR spectrum of EDR respectively, and the respiratory non-rhythmic component, the respiratory rhythmic component, the fundamental rhythmic frequency, the multiple of the fundamental rhythmic frequency, the RRI power in the fundamental rhythmic frequency, or the RRI power in a multiple of the fundamental rhythmic frequency are derived from the MTFR spectrum of RRI and the MTFR spectrum of EDR.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 6 is an electrocardiography (ECG) lasting 30 seconds under deep anesthesia.

DETAILED DESCRIPTION OF THE PREFERRED EMBODIMENTS

Figure 1:
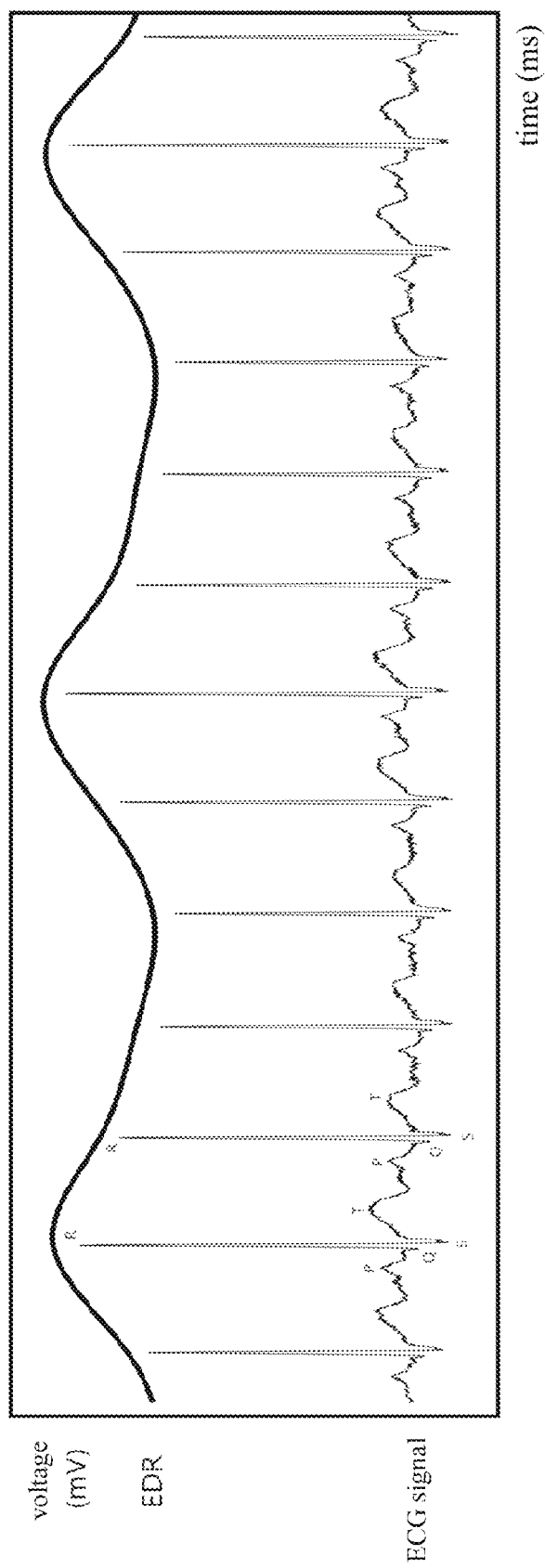
FIG. 1 is an electrocardiograph-derived respiration (EDR) signal to time graph derived from lead III electrocardiographic (ECG) signals.
Figure 2:
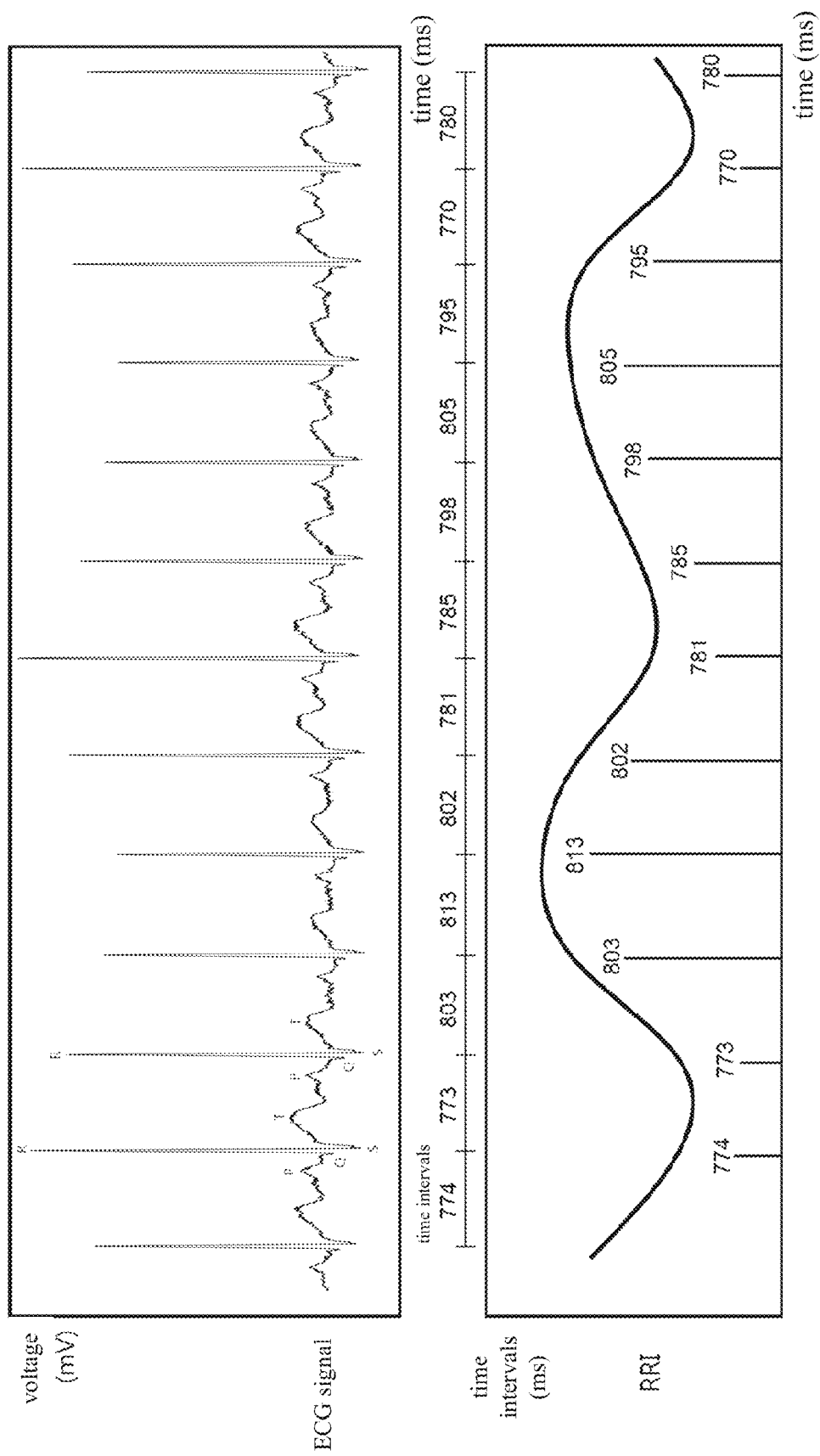
FIG. 2 is an R-R interval (RRI) to time graph derived from lead III electrocardiographic (ECG) signals.

Prior to explaining specific embodiments of the present invention in detail, the principles of the technology and terminology of this invention are introduced first. FIG. 1 and FIG. 2, respectively, are an electrocardiograph-derived respiration (EDR) signal to time graph and an R-R interval (RRI) to time graph derived from lead III electrocardiographic (ECG) signals. The wave below in FIG. 1 is ECG signals, the X-axis is time (millisecond, mS), and the Y-axis is voltage (millivolt, mV). A group of P wave, Q wave, R wave, S wave, and T wave is generated by each heartbeat, in which R wave is a peak with a maximum amplitude in a group. However, the absolute height of R wave by each heartbeat is different. This is because the ECG electrodes are attached to the chest of a subject, and lifted up and lowered down with respiratory cycles, resulting in the absolute heights of R waves in ECG signals fluctuating. Hence, by linking the absolute heights of R waves with a line, the waves of the line representing respiratory patterns are acquired and known as electrocardiography-derived respiration signal (EDR), as shown by the waves above in FIG. 1. Nevertheless, EDR can be calculated or derived by many methods, such as using a fluctuating ECG baseline as EDR, or using other algorithms to calculate and obtain EDR. Although the absolute heights of R waves are used as EDR in the embodiment of the present invention, it is only an exemplary implementation, and should not be regarded as limiting. Referring to the ECG signals above in FIG. 2, the time interval between two adjacent R waves are the time interval between two heartbeats, and are known as "R-R interval" (RRI). The timings when R waves occur are used for the X axis (millisecond, mS), R-R wave intervals are used for the Y-axis (microsecond, mS), and an RRI to time graph can be obtained, as shown by the waves below in FIG. 2, from which information about heart rates and heart rate variability (HRV) can be derived.

Figure 3:
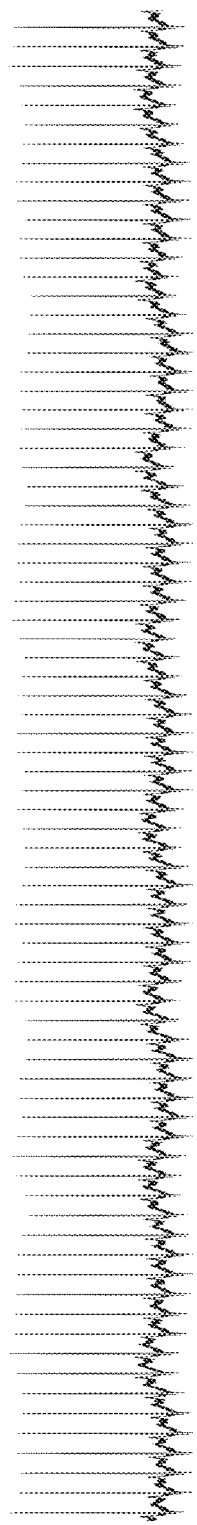
FIG. 3 is an electrocardiography (ECG) lasting 30 seconds under mild anesthesia.
Figure 4A:
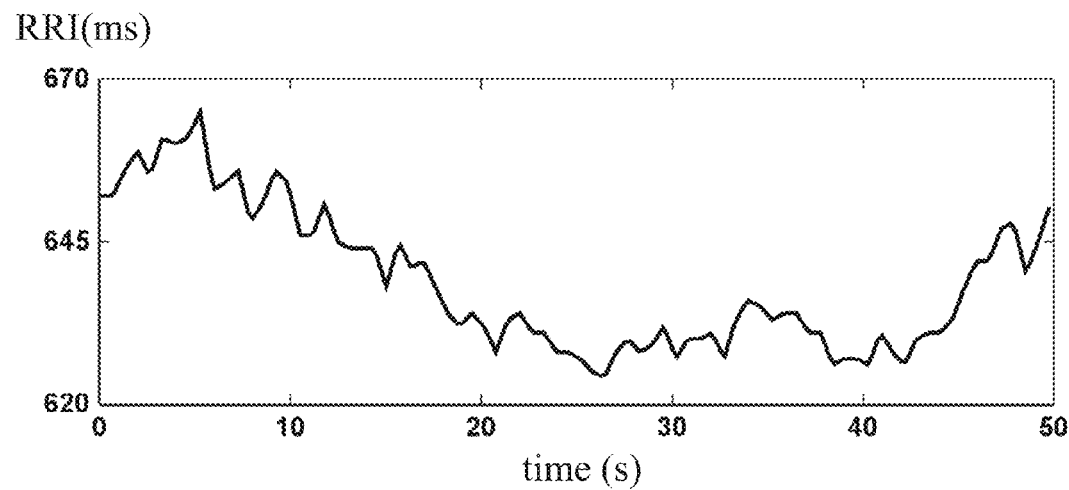
FIG. 4A is an RRI to time graph derived from the ECG of FIG. 3.
Figure 4B:
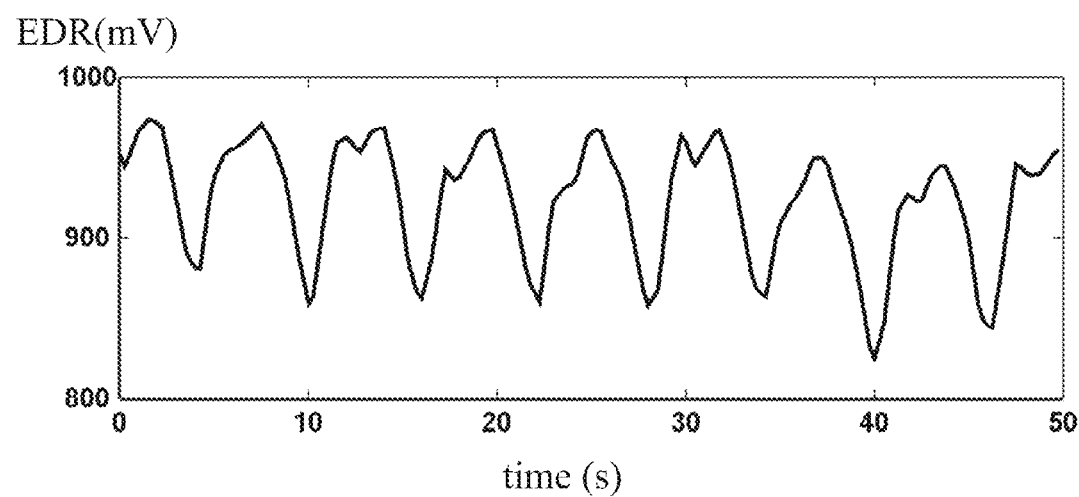
FIG. 4B is an EDR to time graph derived from the ECG of FIG. 3.
Figure 5A:
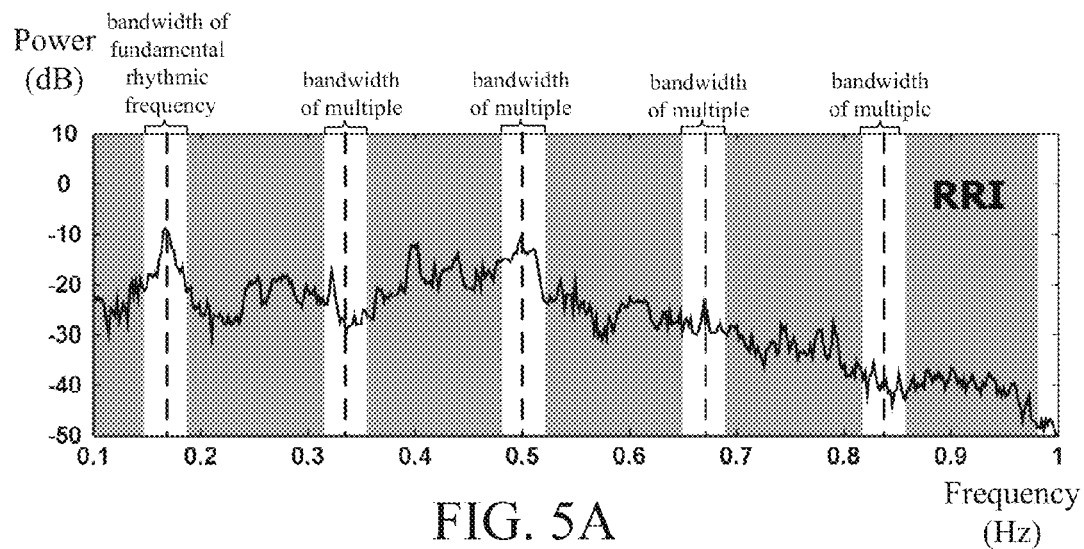
FIG. 5A is a frequency to power spectrum of RRI obtained from an RRI to time graph of FIG. 4A through Fourier transformation.
Figure 5B:
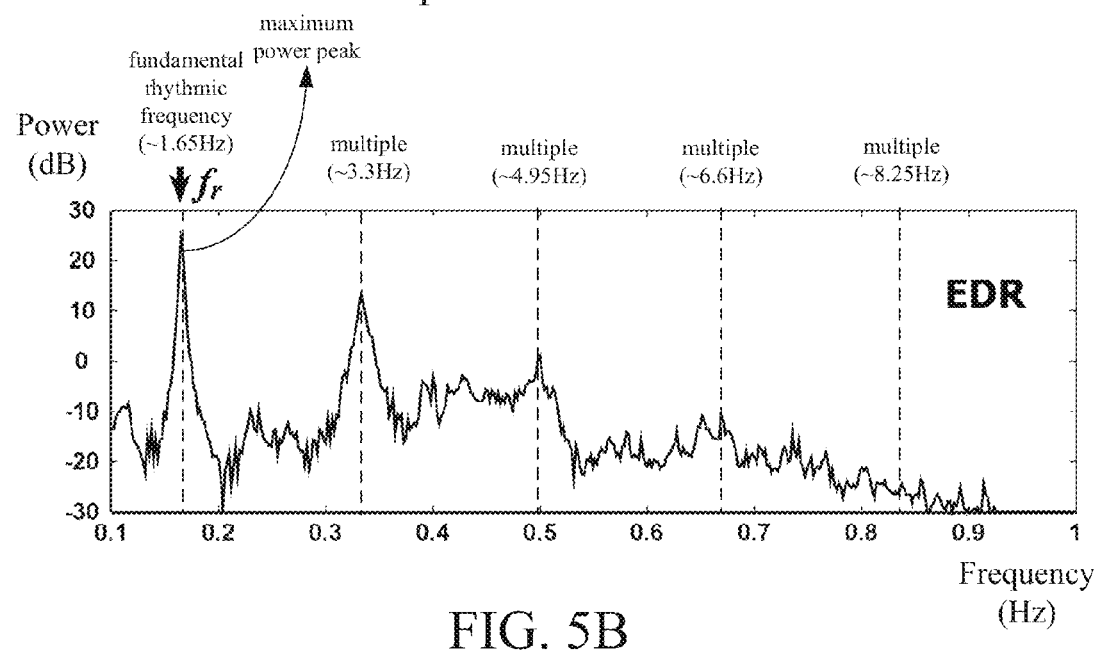
FIG. 5B is a frequency to power spectrum of EDR obtained from an EDR to time graph of FIG. 4B through Fourier transformation.

FIG. 3 and FIG. 6 are electrocardiographies (ECG) lasting 30 seconds under mild anesthesia and under deep anesthesia respectively. Based on the methods discussed above in FIG. 1 and FIG. 2, an RRI to time graph is derived, as shown in FIG. 4A (mild anesthesia) and FIG. 7A (deep anesthesia), and an EDR to time graph is derived, as shown in FIG. 4B (mild anesthesia) and FIG. 7B (deep anesthesia). Frequency to power spectrums of RRI can be obtained from the RRI to time graphs of FIG. 4A and FIG. 7A through Fourier transformation, as shown in FIG. 5A (mild anesthesia) and FIG. 8A (deep anesthesia). Frequency to power spectrums of EDR can be obtained from the EDR to time graphs of FIG. 4B and FIG. 7B through Fourier transformation, as shown in FIG. 5B (mild anesthesia) and FIG. 8B (deep anesthesia). The details are described as follows.

Figure 7A:
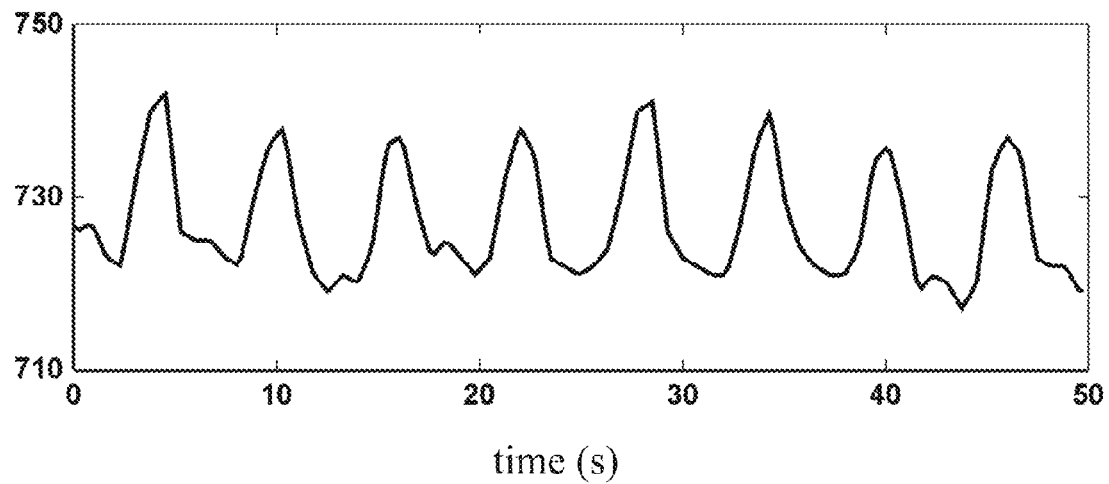
FIG. 7A is an RRI to time graph derived from the ECG of FIG. 6.
Figure 7B:
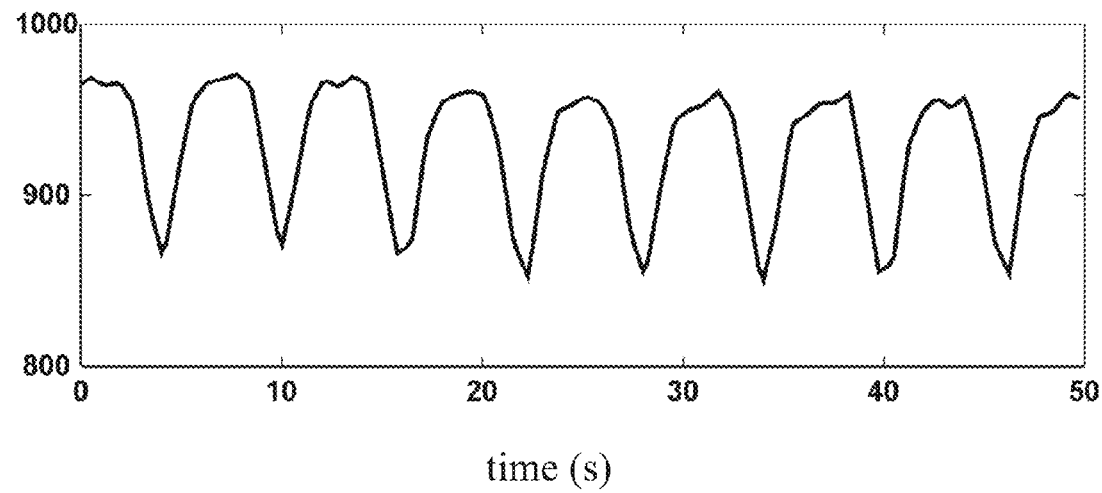
FIG. 7B is an EDR to time graph derived from the ECG of FIG. 6.
Figure 8A:
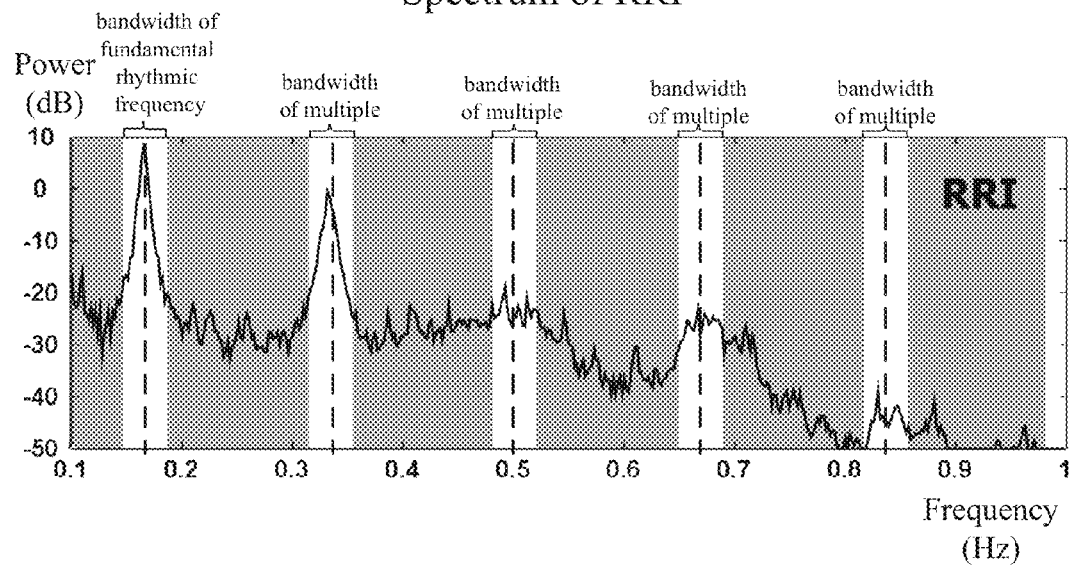
FIG. 8A is a frequency to power spectrum of RRI obtained from an RRI to time graph of FIG. 7A through Fourier transformation.
Figure 8B:
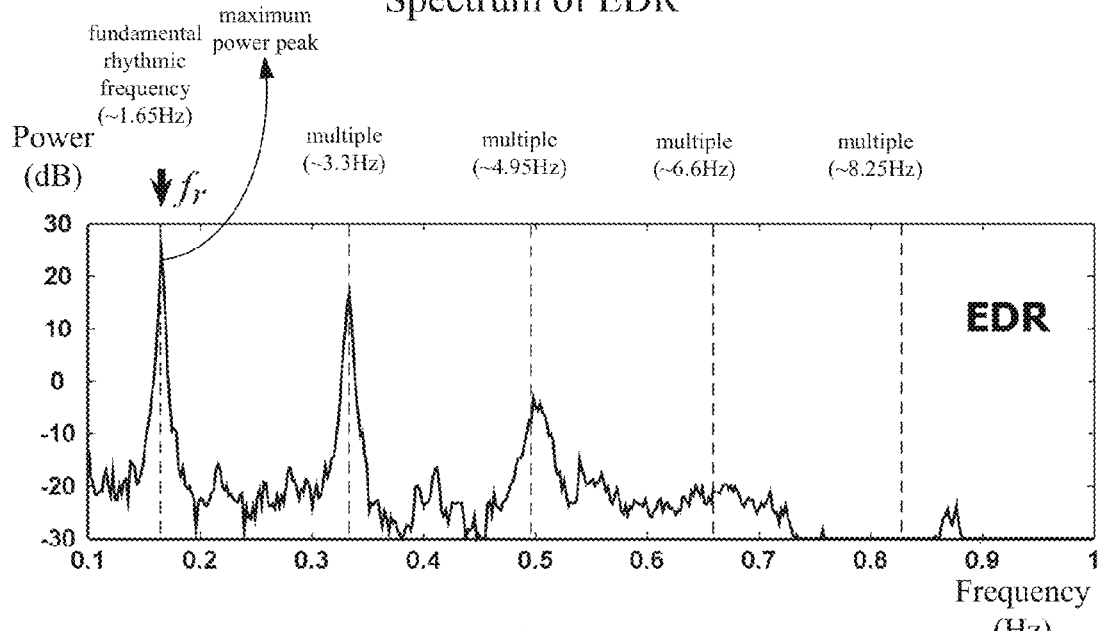
FIG. 8B is a frequency to power spectrum of EDR obtained from an EDR to time graph of FIG. 7B through Fourier transformation.

Respiratory sinus arrhythmia (RSA) is a normal physiological phenomenon that heart rate variability (HRV) is synchronized with respiration. Specifically, heart rates increase during inspiration, and the time intervals between two adjacent heartbeats are shortened (shorten RRI), whereas heart rates decrease during expiration, the time intervals between two adjacent heartbeats are elongated (elongated RRI). The reasons why this phenomenon occurs are related to variation of blood volumes flowing back to the heart and suppression of the vagus nerve resulting from respiration. This physiological phenomenon is commonly observed in humans and many animals. Furthermore, the regularity of respiratory sinus arrhythmia increases with depth of anesthesia. The regularity includes regularity of respiratory patterns and regularity of heart rate variability (HRV). In other words, under deep anesthesia, respiratory sinus arrhythmia (RSA) results in respiration and heart rate variability (HRV) with more rhythmic or regular patterns, while under mild anesthesia, respiratory sinus arrhythmia (RSA) makes respiration and heart rate variability (HRV) non-rhythmic or irregular. Notably, RSA regularity is different from RSA amplitudes, frequencies and extents. For example, fast breath rates or deep breaths do not necessarily mean regular breaths, and fast heart rates, great amplitudes of ECG signals or great heart rate variability (HRV) do not necessarily mean heart rates vary regularly. The possible reason why the regularity of respiratory sinus arrhythmia increases with depth of anesthesia is described as follows: the neural respiratory control is composed by two control systems, which respectively are the control system mediated by the pontomedullary areas and the control system located in the forebrain. The control system located in the pontomedullary areas is autonomous, involuntary respiratory center, which is not controlled by an individual's consciousness, and can emit signals for regular respiration, whereas the control system located in the forebrain is voluntary, can be controlled by an individual's consciousness, and carries out irregular respiration. The anatomies of the two control systems have such significant differences that respiratory signals emitted by the two systems compete with each other and are integrated at the spinal level to control the respiratory motor neurons. Under deep anesthesia, since the control system located in the forebrain, such as the thalamus, and the subcortical regions, is more sensitive to anesthetics, irregular respiration is suppressed, and regular respiratory patterns appear. As to heart rates, the sinus node located in the right atrium of the heart emits regular signals, so that the heart beats regularly, and is not under the control of an individual's consciousness. However, a variety of factors still cause heart rates to vary, such as nerve systems, blood pressure, endocrines, blood volume, blood flow impedance, and respiration. Under mild anesthesia, a number of factors affect the heart rate, making the heart rate variability (HRV) irregular, as shown in FIG. 4A. The heart rate varies irregularly (irregular HRV) in the RRI to time graph, and the relationship between HRV and respiratory patterns in the EDR to time graph are not obvious, as shown in FIG. 4A and FIG. 4B. Under deep anesthesia, since respiratory frequencies and wavelengths are unified, as shown in FIG. 7B, the effects of respiration on HRV suddenly increase, the heart rate varies regularly, causing HRV with an obvious and regular waveform, as shown in FIG. 7A. Furthermore, the waveform is synchronized with the respiratory pattern. Both share the same wavelength and frequency (about 0.165 Hz, times/sec), which is known as the respiratory frequency or respiratory rate. It shows that in the case of deep anesthesia, respiration becomes a major factor affecting HRV, and effects of other factors on HRV are relatively less. Since the waves in RRI and EDR to time graphs always have the same frequency, which is the respiratory frequency, after Fourier transformation, the maximum power peak of RRI and the maximum power peak of EDR are found at the respiratory frequency (0.165 Hz), and the power peaks of RRI and the power peaks of EDR are also found at multiples of the respiratory frequency (0.33, 0.495, 0.66, 0.825 Hz) in the frequency to power spectrums of RRI and EDR, as shown in FIG. 8A and FIG. 8B, respectively. In contrast, under mild anesthesia, no regular waveform of RRI, consistent frequency of RRI, and distinct relationship between RRI and EDR can be observed in the RRI to time graph and the EDR to time graph, as shown in FIG. 4A and FIG. 4B. Therefore, after the Fourier transformation, although the high power peaks of EDR are still observed at the respiratory frequency (at 0.165 Hz) and its multiples (at 0.33, 0.495, 0.66, 0.825 Hz), as shown in the frequency to power spectrum of RRI of FIG. 5B, the power peaks of RRI at the respiratory frequency (at 0.165 Hz) and its multiples (0.33, 0.495, 0.66, 0.825 Hz) are not significant, as shown in the frequency to power spectrum of FIG. 5A, and significantly lower than the power peaks of the corresponding frequencies under deep anesthesia in FIG. 8A.

In conclusion, the deeper the anesthesia is, the more the regular respiratory pattern is as shown in the EDR to time graphs in FIG. 4B and FIG. 7B, which means that the wavelengths and frequencies of EDR are more unified, and then the extent of HRV affected by respiration increases. Hence, the more the waves of RRI are synchronized with the respiratory patterns or EDR as shown in the RRI to time graphs of FIG. 4A and FIG. 7A, after Fourier transformation, the higher the power peaks of RRI at the respiratory frequency and its multiples are, as shown in the frequency to time spectrums of RRI of FIG. 5A and FIG. 8A.

Therefore, the power at the respiratory frequency and its multiples (in white areas) represents the extent of HRV affected by respiration, and "a respiratory rhythmic component" is defined as a value representing the extent of HRV affected by respiration. On the contrary, the power at other frequencies (in grey areas) represents the extent of HRV not affected by respiration as shown in the frequency to power spectrums of RRI of FIG. 5A and FIG. 8A, and "a respiratory non-rhythmic component" is defined as a value representing the extent of HRV not affected by respiration. Thus, a ratio of the power at the respiratory frequency and its multiples (respiratory rhythmic component) to the power at other frequencies (respiratory non-rhythmic component) represents regularity of RSA, and can be used for estimating depth of anesthesia.

First Embodiment of the Method for Estimating Depth of Anesthesia

Figure 9:
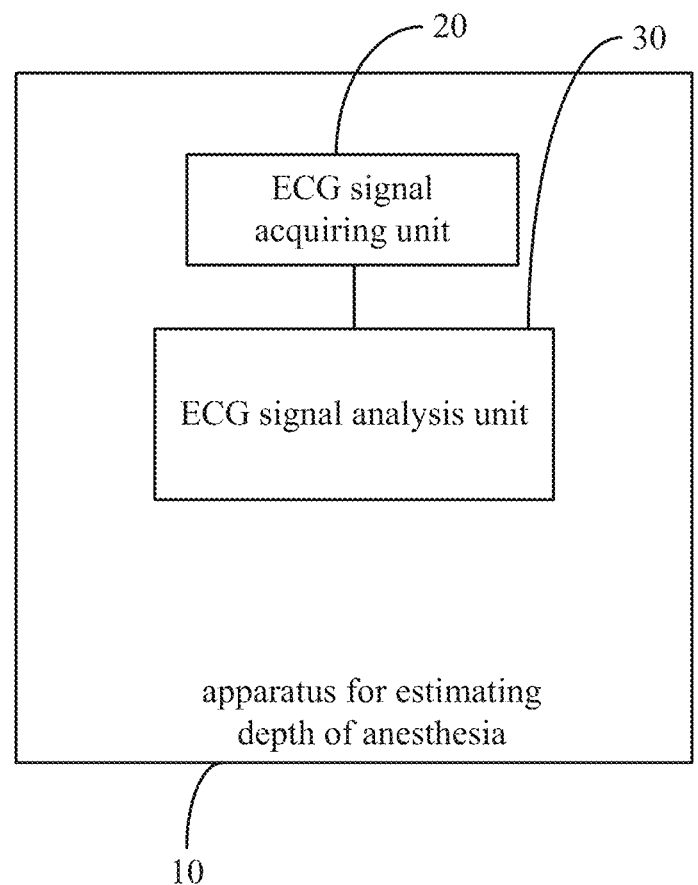
FIG. 9 is a schematic diagram illustrating an apparatus of the present invention for estimating depth of anesthesia.
Figure 10:
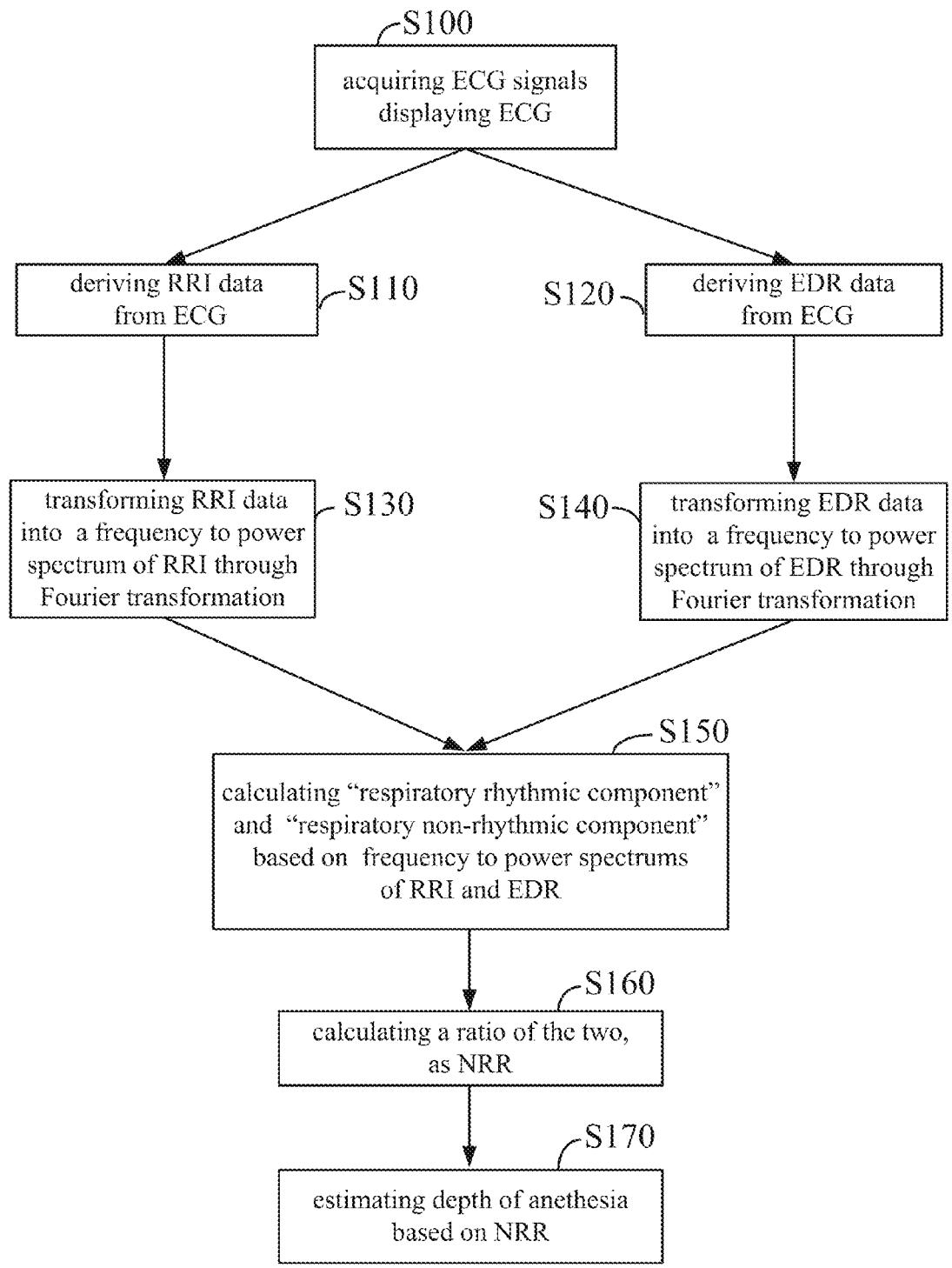
FIG. 10 is a flow chart illustrating a method for estimating depth of anesthesia in accordance with a first embodiment of the present invention.

FIG. 9 and FIG. 10 are respectively a schematic diagram illustrating an apparatus for estimating depth of anesthesia 10 in this invention and a flow chart illustrating a method for estimating depth of anesthesia in accordance with a first embodiment of the present invention. The apparatus for estimating depth of anesthesia 10 includes an ECG signal acquiring unit 20 and an ECG signal analysis unit 30, which is coupled with the ECG signal acquiring unit 20. The ECG signal acquiring unit 20 has one or more electrodes (not shown).

In step S100, the ECG signal acquiring unit 20 acquires ECG signals from a subject via the electrodes in a non-intrusive way, and then outputs digitized ECG signals to the ECG signal analysis unit 30. After receiving the digitized ECG signals, the ECG signal analysis unit 30 plots an electrocardiography (ECG).

The ECG signal acquiring unit 20 and the ECG signal analysis unit 30 detect and record the ECG signals from the heart in three different directions by using the lead I, lead II, and lead III ECG, in order to improve accuracy. However, this does not mean that the use of single-lead ECG is not feasible, and should not be regarded as limiting. If finding ectopic beats or severe ECG signal interferences, the ECG signal analysis unit 30 will remove and discard the data segment. Afterward, the ECG signal analysis unit 30 derives RRI data and EDR data from the ECG in step S110 and step S120 respectively according to the method described above. Both of step S110 and steps S120 can be performed in any order or simultaneously. The ECG signal analysis unit 30 transforms the RRI data and EDR data into a frequency to power spectrum of RRI and a frequency to power spectrum of EDR respectively through Fourier transformation, such as Hanning window and 1024 point fast Fourier transform, as shown in step S130 and step S140. Both step S110 and step S120 can be performed in any order or simultaneously. The ECG signal analysis unit 30 calculates a "respiratory rhythmic component" and a "respiratory non-rhythmic component" based on the frequency to power spectrums of RRI and EDR, as shown in step S150.

The exact calculation is described as follows: a maximum power peak of EDR exists in a specific frequency range in the frequency to power spectrum of EDR, e.g. 0-1 Hz, as shown in FIG. 5B and FIG. 8B. A frequency to which the maximum power peak corresponds is representative of the exact value of the respiratory frequency of the subject, which herein is called a "fundamental rhythmic frequency". Subsequently, in a specific frequency range of the frequency to power spectrum of RRI, e.g. 0-1 Hz, as shown in FIG. 5A and FIG. 8A, the sum of RRI power in a specific bandwidth, e.g. ±0.02 Hz, where the fundamental rhythmic frequency is located and RRI power in specific bandwidths, e.g. ±0.02 Hz, where multiples of the fundamental rhythmic frequency are located is calculated. The sum is defined as the respiratory rhythmic component. Thus, RRI and EDR are required in the calculation of the respiratory rhythmic component, which the frequency to power spectrum of EDR is used for identifying the fundamental rhythmic frequency of the respiratory rhythmic component, while the frequency to power spectrum of RRI is used for calculating the respiratory rhythmic component. In contrast, in this embodiment, the exact calculation of the respiratory non-rhythmic component is described as follows: total RRI power in a specific frequency range, e.g. 0-1 Hz, in the same frequency to power spectrum of RRI subtracted by the respiratory rhythmic component. Afterwards, a ratio of the non-respiratory rhythmic component to the respiratory rhythmic component is used as an index, which is named as a "non-rhythmic to rhythmic ratio" or NRR, as shown in step S160. The non-rhythmic to rhythmic ratio or NRR can be used for representing the regularity of respiratory sinus arrhythmia (RSA), and then estimating depth of anesthesia, as shown in step S170. The above procedures can be achieved by using commercially available software, such as Microsoft Visual Studio®.

Second Embodiment of the Method for Estimating Depth of Anesthesia

On the basis of the first embodiment, multitaper time-frequency reassignment (MTFR) can be further applied to replace the method of Fourier transformation. MTFR is a time-frequency analysis combining two techniques, the time-frequency reassignment technique and the multitaper technique. The reassignment technique significantly improves resolution of spectrums, and the multitaper technique suppresses variation of spectrums Based on these two techniques, an RRI to time graph and an EDR to time graph are transformed into frequency to power spectrums of RRI and EDR with higher resolution. Therefore, a more precise respiratory rhythmic component, a respiratory non-rhythmic component and NRR can be calculated and obtained from the spectrums, and thereby the RSA regularity is effectively quantified. Herein, the spectrums derived from the multitaper time-frequency reassignment are called MTFR spectrums. More details of the MTFR analysis are described in the following references: Francois Auger and Patrick Flandrin, "Improving the readability of time-frequency and time-scale representations by the reassignment method", IEEE Trans Signal Process (1995), and Xiao Jun and Patrick Flandrin, "Multitaper Time-Frequency Reassignment for Nonstationary Spectrum Estimation and Chirp Enhancement", IEEE Trans Signal Process Journal (2007).

Figure 11:
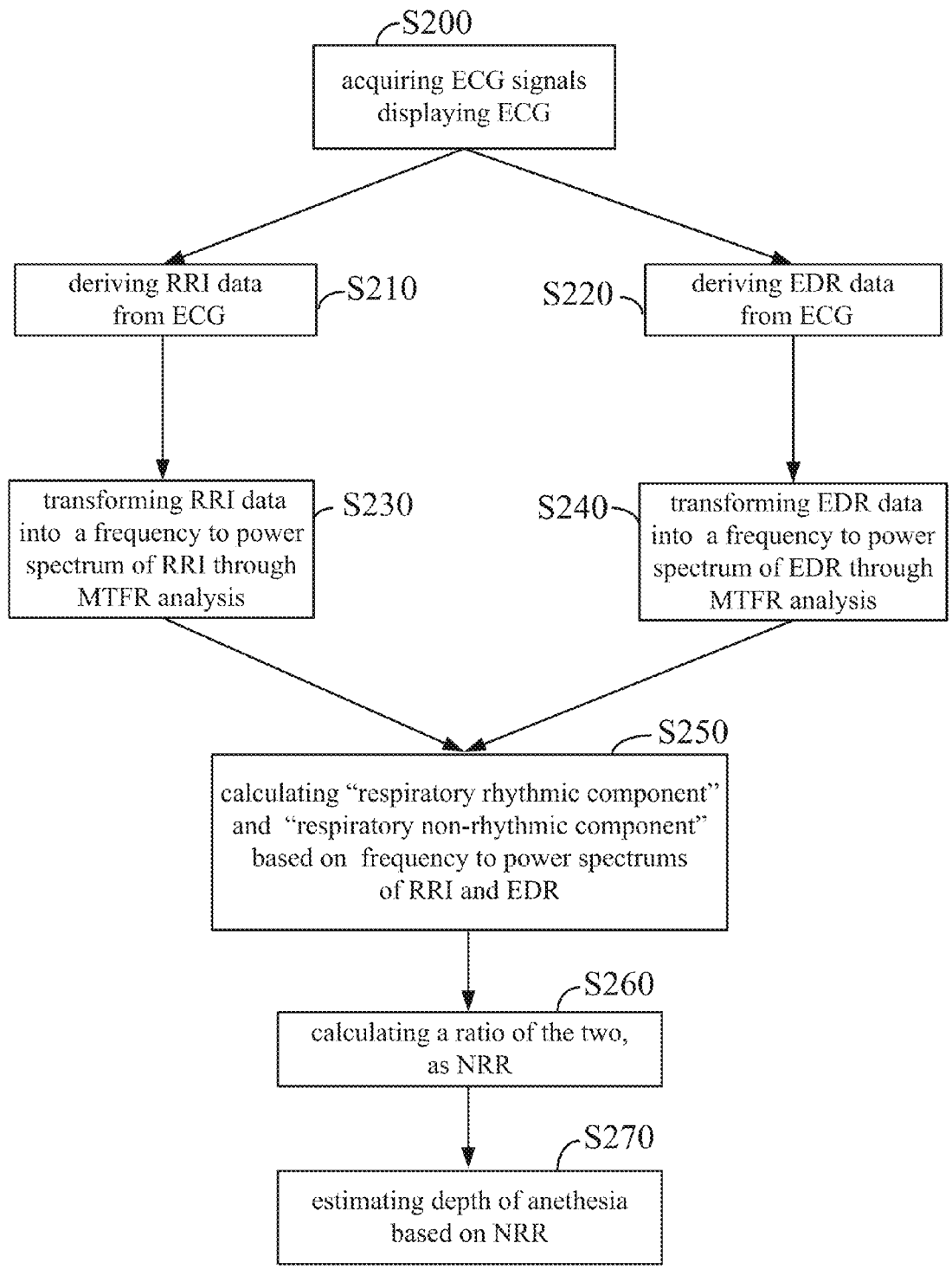
FIG. 11 is a flow chart illustrating a method for estimating depth of anesthesia in accordance with a second embodiment of the present invention.

FIG. 11 is a flow chart illustrating a method for estimating depth of anesthesia in accordance with a second embodiment of the present invention, in which the Fourier transformation in step S130 and step S140 is replaced with the MTFR analysis in step S230 and step S240, and the RRI data and the EDR data are transformed into a frequency to power MTFR spectrum of RRI and a frequency to power MTFR spectrum of EDR. In step S250, according to the frequency to power MTFR spectrums of RRI and EDR, the respiratory rhythmic component and the respiratory non-rhythmic component are calculated. The exact calculation is described as follows: since an MTFR spectrum is a function of time and frequency, the MTFR spectrums of RRI and EDR are respectively represented as $MTFR_{RRI}(t,f)$ and $MTFR_{EDR}(t,f)$. The MTFR spectrum of EDR, $MTFR_{EDR}(t,f)$ can be used for obtaining the exact value of the fundamental rhythmic frequency $fr(t)$. The definition of the fundamental rhythmic frequency $fr(t)$ is a frequency corresponding to a maximum power peak of EDR in a specific frequency range, e.g. 0-1 Hz, in the MTFR spectrum of EDR, $MTFR_{EDR}(t,f)$. The fundamental rhythmic frequency $fr(t)$ is expressed as follows:

$$f_r(t) = \underset{f \in R^+}{\operatorname{argmax}} MTFR_{EDR}(t,f) \qquad \text{Formula 1}$$

The respiratory rhythmic component $Pr(t)$ is defined as the sum of RRI power in a specific bandwidth, e.g. ±0.02 Hz, where the fundamental rhythmic frequency is located and RRI power in specific bandwidths, e.g. ±0.02 Hz, where multiples of the fundamental rhythmic frequency are located in a specific frequency range, e.g. 0-1 Hz, in the frequency to power spectrum of RRI, $MTFR_{RRI}(t,f)$. The respiratory rhythmic component $Pr(t)$ is expressed as follows:

$$P_r(t) = \sum_{n=1}^{k} \int_{n \cdot f_r - bHz}^{n \cdot f_r + bHz} MTFR_{RRI}(t,f) df \text{ for } k \cdot f_r < aHz \qquad \text{Formula 2}$$

a is a maximum frequency value to define the specific frequency range. a=1 in this embodiment. k represents the highest integer, and fr is the fundamental rhythmic frequency, so that k·fr within the specific frequency range. In this embodiment, since a=1, 0<k·fr<1, which means that the maximum multiple of the fundamental rhythmic frequency is not greater than 1 Hz. b defines the specific bandwidth. In this embodiment, b is 0.02, so the specific bandwidths are ±0.02 Hz. The respiratory non-rhythmic component is defined as total RRI power in the specific frequency range, e.g. 0-1 Hz, in the frequency to power spectrum of RRI subtracted by the respiratory rhythmic component. Based on the respiratory non-rhythmic component and the respiratory rhythmic component derived from the MTFR spectrums of RRI and EDR, a ratio of the two are calculated and defined as the "non-rhythmic to rhythmic ratio" or NRR, as shown in step S260. NRR is calculated as follows:

$$NRR(t) = \log_{10}\left(\frac{HF_{MR}(t) - P_r(t)}{P_r(t)}\right) \quad \text{Formula 3}$$

$HF_{MR}$ (t) is RRI total power in the specific frequency range in the MTFR spectrum of RRI. The remaining steps of the second embodiment are substantially the same as the first embodiment. Notably, in the following clinical experiments, the method for estimating depth of anesthesia by using ECG is performed based on the MTFR analysis in the second embodiment of the present invention, for obtaining more precise data.

Experiments of the Correlation between NRR and Anesthetics and the Ability to Predict Anesthetic Events Standard anesthetic monitoring (HP agilent patient monitor system), including Bispectral Index Monitors® (BIS monitor), ECG, pulse oximetry (SpO2), and non-invasive blood pressure, are applied to all subjects. Anesthetic induction begins with fentanyl 2.5-3 μg/kg. After preoxygenation, hypnosis is induced with propofol 2-2.5 mg/kg. Loss of consciousness (LOC) is assessed every 10 seconds by either no response to verbal command or loss of eyelash reflex. Cisatracurium 0.15 mg/kg is used to facilitate tracheal intubation. Subsequently, mechanical ventilation is started from volume control mode with oxygen-gas-sevoflurane mixture as low flow anesthesia. The tidal volume is 7 mL/kg in the beginning and ventilator rate was between 8 to 16 breaths per minute. The ventilator is adjusted to maintain an end-tidal carbon oxide ($ETCO_2$) between 35 to 40 mmHg and to keep the peak airway pressure lower than 25 mm Hg. Surgical skin incision is made by a blade after adequate depth of anesthesia is achieved. Skin wound closure is identified as the near end of surgery, when the anesthetic gas is gradually decreased. Muscle relaxation is reversed with a combination of neostigmine 0.05 mg/kg and glycopyrrolate 0.01 mg/kg during controlled ventilation. When the subject regains adequate spontaneous breathing, controlled ventilation is stopped. Subjects showing inadequate spontaneous breathing ($ETCO_2$ more than 50 mmHg or $SpO_2$ less than 95%) are assisted with manual positive ventilation, otherwise spontaneous breathing is allowed until regaining consciousness without the interference of positive-pressure ventilation. The endotracheal tube is removed when the subject showed adequate spontaneous breathing. Corrective actions including mask ventilation or nasopharyngeal airway insertion are given in cases of inadequate ventilation or upper airway obstruction after extubation. During the emergence period, first reaction is assessed as any visible motor reactions such as movement of the arms or legs, coughing or grimacing. After first reaction, return of consciousness (ROC) is assessed every 20 seconds for opening of eyes and ability to follow simple commands. The surgical procedures and medicine dosages described above are only exemplary embodiments. The method and apparatus for estimating depth of anesthesia in this invention are applicable to other surgical procedures and medicine dosage, and consequently should not be regarded as limiting.

The inhaled and end-tidal concentrations of anesthetic gas detected by the gas analyzer on a Datex-Ohmeda S/5 anesthesia machine (GE Health Care, Helsinki, Finland) are also recorded every 30 seconds. The estimated effect-site sevoflurane concentration ($C_{eff}$) is derived from the end-tidal sevoflurane concentration ($C_{et}$) by the following first order differential equation, which is based on the pharmacokinetic-pharmacodynamic modeling:

$$\frac{dC_{eff}}{dt} = K_{e0}(C_{et} - C_{eff}) \quad \text{Formula 4}$$

The constant $K_{e0}$ is assumed to be constant for all subjects and defined as 0.24/min according to previous studies. In addition, the timestamps of anesthetic events are recorded, including induction, LOC, skin incision, first reaction and ROC. Recordings were ended after ROC. The BIS index is recorded every five seconds from an Aspect A-2000 BIS monitor. The raw ECG signals of Lead I, II, and III are sampled at 1000 Hz and 12-bit resolution, recorded and analyzed in the method of the second embodiment described above for obtaining NRR. Furthermore, the MTFR spectrum of RRI is used to quantify the corresponding indices derived from HRV, including time-varying high frequency power ($HF_{MR}$), time-varying low frequency power ($LF_{MR}$) and time-varying $LF_{MR}$ to $HF_{MR}$ ratio ($LHR_{MR}$) respectively. These indices are parallel to the classical frequency domain HRV parameters, including high frequency power ($HF_{PS}$), low frequency power ($LF_{PS}$), and $LF_{PS}$ to $HF_{PS}$ ratio ($LHR_{PS}$), which which are quantified by the classic Fourier transformation. The measurement parameters described above are only exemplary embodiments. The method and apparatus for estimating depth of anesthesia in this invention are applicable to other measurement parameters, and consequently should not be regarded as limiting.

BIS index and ECG-derived continuous indices are taken, including NRR, $HF_{MR}$, $LF_{MR}$ $LHR_{MR}$, and HR, as indices of depth of anesthesia. The performances of the indices are evaluated in two aspects: their correlations with effect-site sevoflurane concentration and their ability to predict anesthetic events. The correlation with sevoflurane concentration employs prediction probability ($P_K$) analysis and Spearman rank correlation. The ability to predict anesthetic events is investigated by serial $P_K$ (analysis. A p value less than 0.05 is considered as statistically significant. Statistical results are expressed as mean (standard deviation [SD]). $P_K$ analysis is a versatile statistic method measuring the performance of an anesthetic depth index. A value of 1 means that the indicator always correctly predicts the observed depth of anesthesia, a value of 0.5 means that the indicator predicts no better than 50/50 chance, and a $P_K$ value less than 0.5 means that the indicator predicts inversely. To be more precise, a 0 value also means a perfect prediction but in a reversed direction. $P_K$ analysis can be applied to paired data or continuous data without the limitation of unit, scale or distributional assumption of the data. Estimation of $P_K$ and its standard error is obtained by the Jackknife method. Before the null hypothesis, $P_K$ value less than 0.5 is converted into 1 minus the $P_K$ value.

Correlation between the above indices and sevoflurane concentration is investigated in the emergence period. The time interval when the sevoflurane concentration monotonically and continuously decreased is selected. The period of controlled ventilation is from the start of decreasing sevoflurane concentration to the end of controlled ventilation. The period of spontaneous breathing is from the start of adequate spontaneous breath to ROC. Data from these two periods are evaluated separately because the physiological mechanisms affecting RSA are different. $P_K$ analysis and Spearman rank correlation are employed to analyze performance of indices sampled every 4 seconds. The results are tabulated as weighted averages according to each subject's data length. The bootstrap method is used to calculate the 95% confidence interval of Spearman correlation based on 10,000 samplings. A value of Spearman correlation closer to −1 is better since the indices increase to correlate with the decrease of sevoflurane concentration.

To evaluate the performance of the anesthetic indices in predicting the anesthetic events, serial $P_K$ analysis is used as shown in a previous study. The following timestamps are defined as the baseline: one minute before LOC, five seconds before skin incision, three minutes before the first reaction, and three minutes before ROC. The serial $P_K$ analysis is performed by analyzing data pairs on successive timestamps spaced by five seconds. As a result, the output of serial $P_K$ analysis is a sequence of time-varying $P_K$ values revealing the temporal relation between the anesthetic events and the indices. By plotting the serial $P_K$ value and its standard error bar, the significant difference (p<0.05) can be observed with the naked eye. The significant difference between indices can be established if 1.5 times of their standard error bars do not overlap. In the serial $P_K$ analysis for skin incision, $LF_{PS}$ is also taken into consideration as an index. The statistical analyses described above are only exemplary embodiments. The method and apparatus for estimating depth of anesthesia in this invention are applicable to other statistical analyses, and consequently should not be regarded as limiting.

The correlation with the estimated effect-site sevoflurane concentration is evaluated for two different ventilation methods: controlled ventilation (CV), as shown in table 1, or spontaneous breathing (SB), as shown in table 2, in which the indices marked by*have significant differences from NRR. The data numbers of CV and SB are 4662 and 5810 (18648 s and 23240 s) respectively and average duration per subject is 615±383 s and 750±322 s respectively. The rankings of indices are in general consistent between CV and SB, as well as between $P_K$ analysis and Spearman rank correlation (R). BIS index correlates with effect-site sevoflurane concentration best (CV: $P_K$=0.716, R=−0.575, SB: $P_K$=0.841, R=−0.831, all p value <0.0001). NRR is second (CV: $P_K$=0.670, R=−0.467, SB: $P_K$=0.732, R=−0.565, all p value <0.0001). $LF_{MR}$ is the best HRV indices (CV: $P_K$=0.582 p=0.007, R=−0.233 p=0.004, SB: $P_K$=0.622, r=−0.343, both p value <0.0001). Compared to $LF_{MR}$, NRR is marginally significantly better in CV ($P_K$: p=0.057, R: p=0.006) and significantly better in SB (both p<0.01). BIS index surpasses NRR non-significantly in CV (PK: p=0.48, R: p=0.12), and significantly in SB (both p values<0.001). NRR is significantly better than HR (all p<0.0001).

TABLE 1

|  | $P_K$ (standard error) | Spearman rank correlation (95% confident interval) |
|---|---|---|
| BIS | 0.716 (0.020) | −0.575 (−0.661, −0.476) |
| NRR | 0.670 (0.025) | −0.467 (−0.583, −0.337) |
| $HF_{MR}$ | 0.479 (0.027)* | 0.073 (−0.069, 0.211)* |

TABLE 1-continued

|  | $P_K$ (standard error) | Spearman rank correlation (95% confident interval) |
|---|---|---|
| $LF_{MR}$ | 0.582 (0.025) | −0.233 (−0.359, −0.101)* |
| $LHR_{MR}$ | 0.581 (0.025) | −0.233 (−0.364, −0.096)* |
| Heart Rate | 0.423 (0.024)* | 0.152 (0.034, 0.269)* |

TABLE 2

|  | $P_K$ (standard error) | Spearman rank correlation (95% confident interval) |
|---|---|---|
| BIS index | 0.841 (0.015)* | −0.831 (−0.880, −0.768)* |
| NRR | 0.732 (0.018) | −0.656 (−0.726, −0.568) |
| $HF_{MR}$ | 0.469 (0.023)* | 0.107 (−0.013, 0.223)* |
| $LF_{MR}$ | 0.622 (0.022)* | −0.343 (−0.449, −0.228)* |
| $LHR_{MR}$ | 0.621 (0.021)* | −0.339 (−0.445, −0.224)* |
| Heart Rate | 0.537 (0.024)* | −0.153 (−0.267, −0.03)* |

Figure 12:
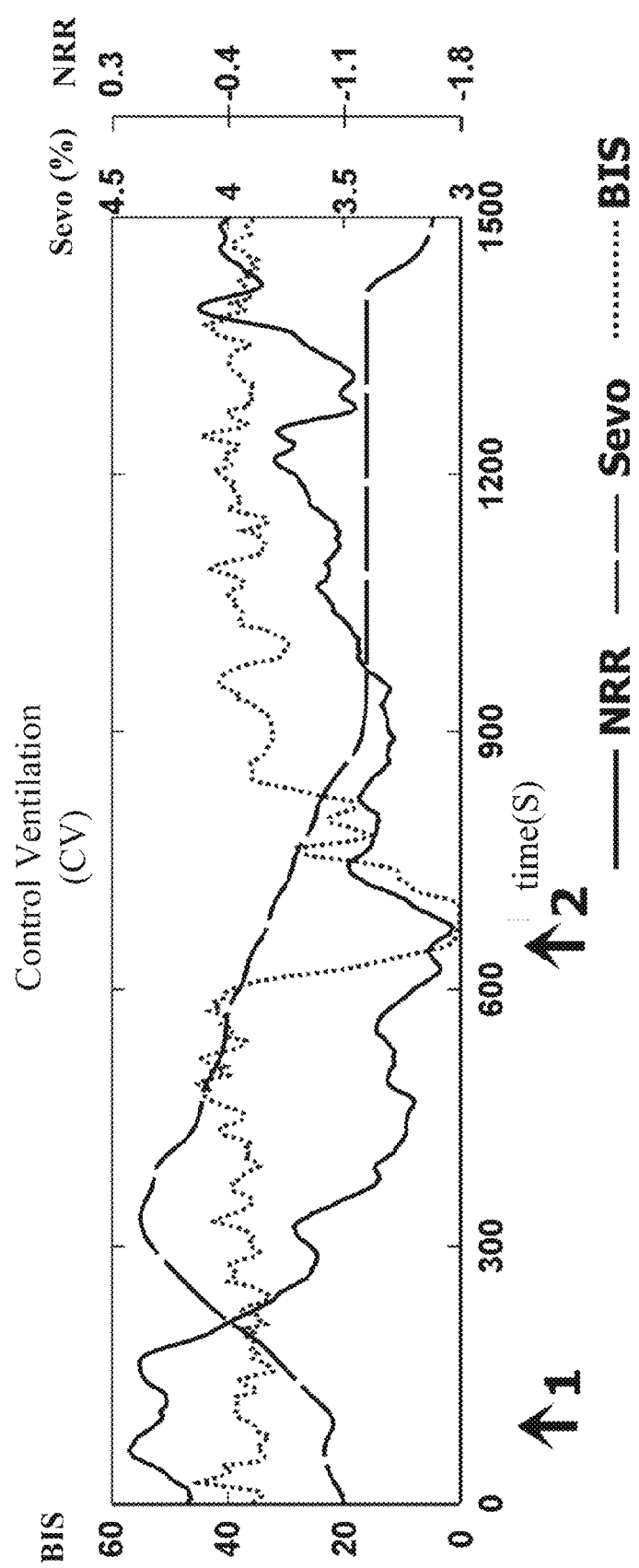
FIG. 12 is a NRR, BIS index and the sevoflurane concentration to time graph, in which the subject is under anesthesia and controlled ventilation.
Figure 13:
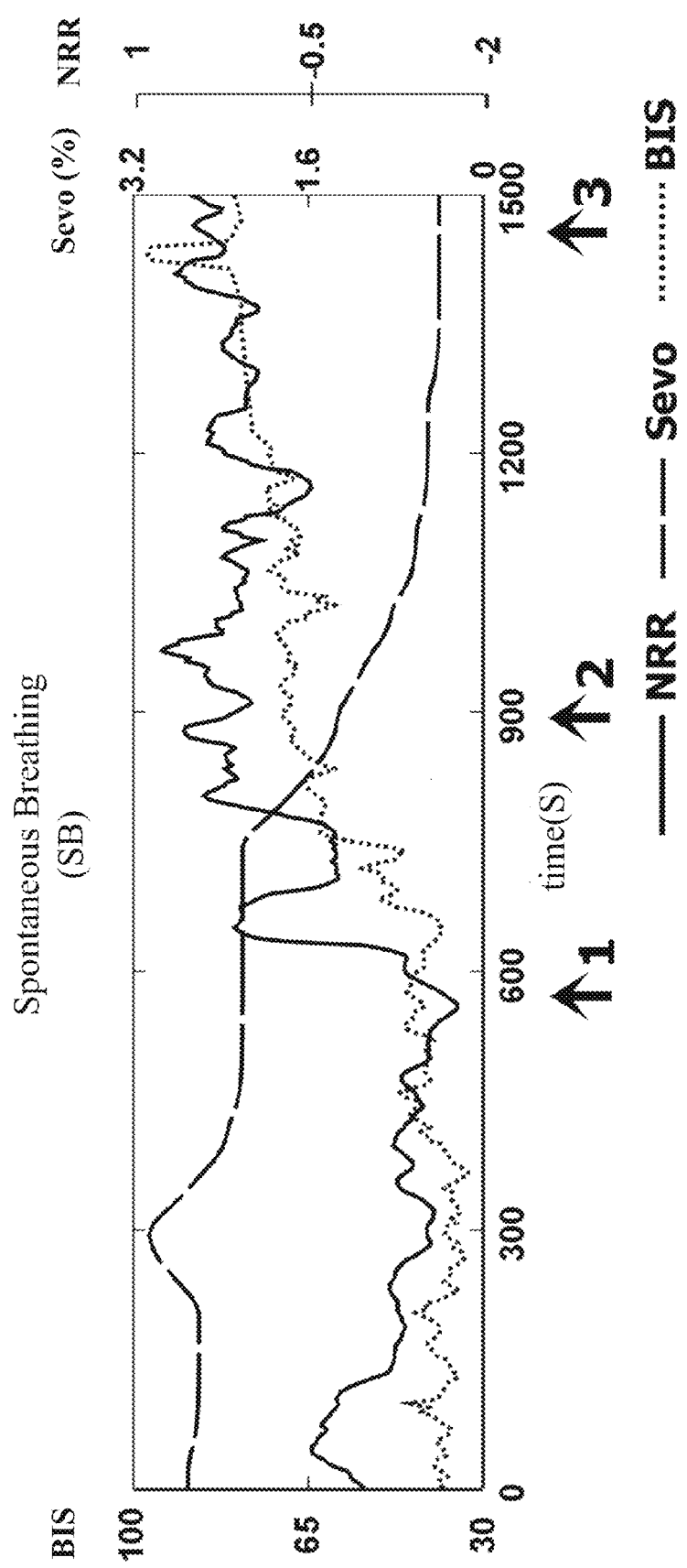
FIG. 13 is a NRR, BIS index and the sevoflurane concentration to time graph, in which the subject is during an emergence period and under spontaneous breathing.

FIG. 12 and FIG. 13 are a NRR, BIS index and the sevoflurane concentration to time graphs. As shown in FIG. 12, the subject is under a condition of anesthesia and controlled ventilation. Arrow 1 shows that an inadequate level of anesthesia is noted, and the sevoflurane concentration is raised. Since lower values of NRR and BIS index refer to deeper anesthesia, arrow 2 shows that both BIS index and NRR reached minimum. As shown in FIG. 13, the subject is during an emergence period and under spontaneous breathing. Arrow 1 shows that endotracheal suction and extubation are performed on the subject. Arrow 2 shows when the subject's first reaction occurs. Arrow 3 shows when the subject's consciousness returns. The concentration of the anesthetic, sevoflurane, gradually decreases during this period, while the NRR and BIS index are gradually increased, showing that both NRR and BIS index both have a high correlation with the concentration of the anesthetic, sevoflurane.

Figure 14:
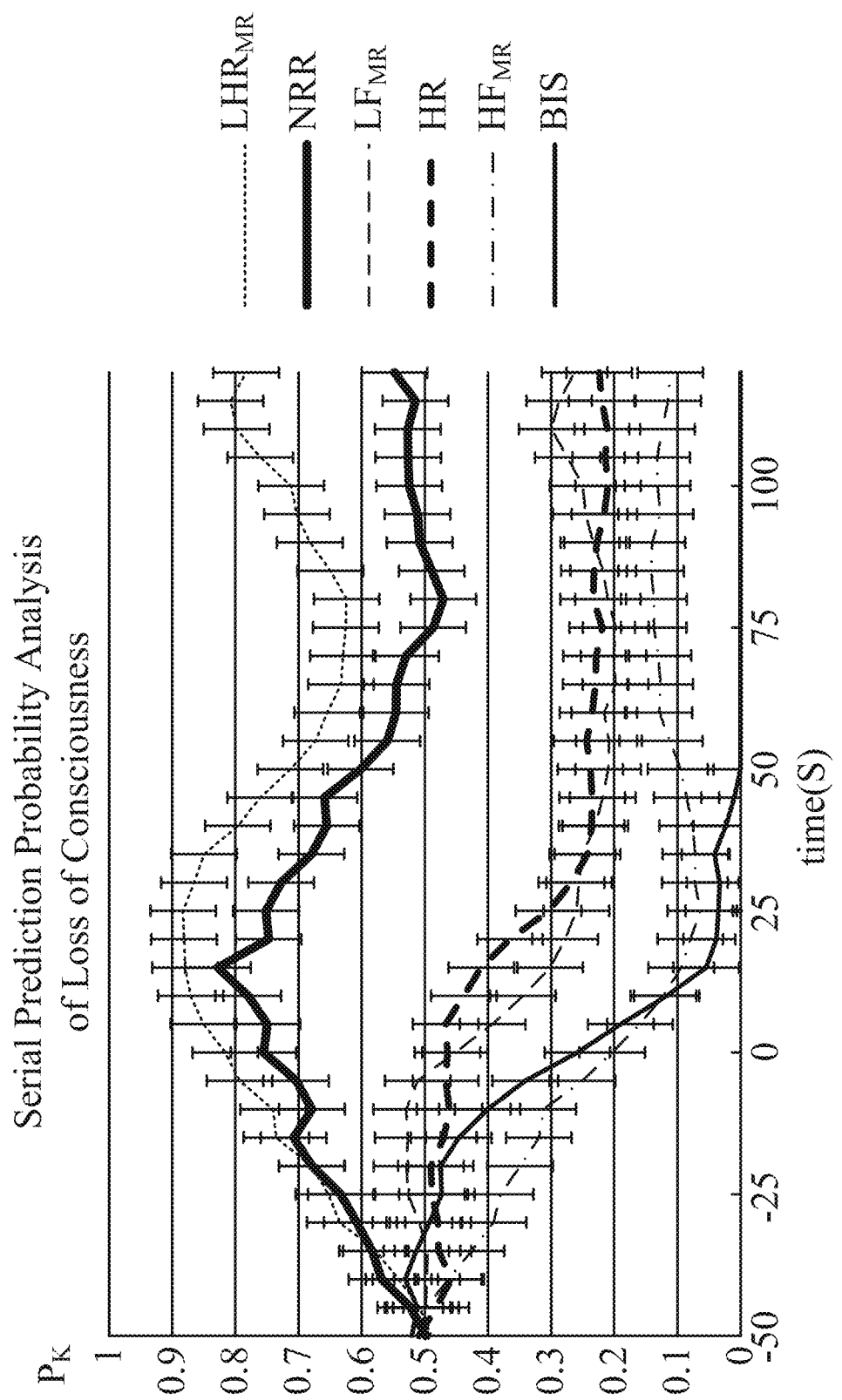
FIG. 14 is a serial Pk value to time graph illustrating the ability of each index predicting loss of consciousness (LOC).
Figure 15:
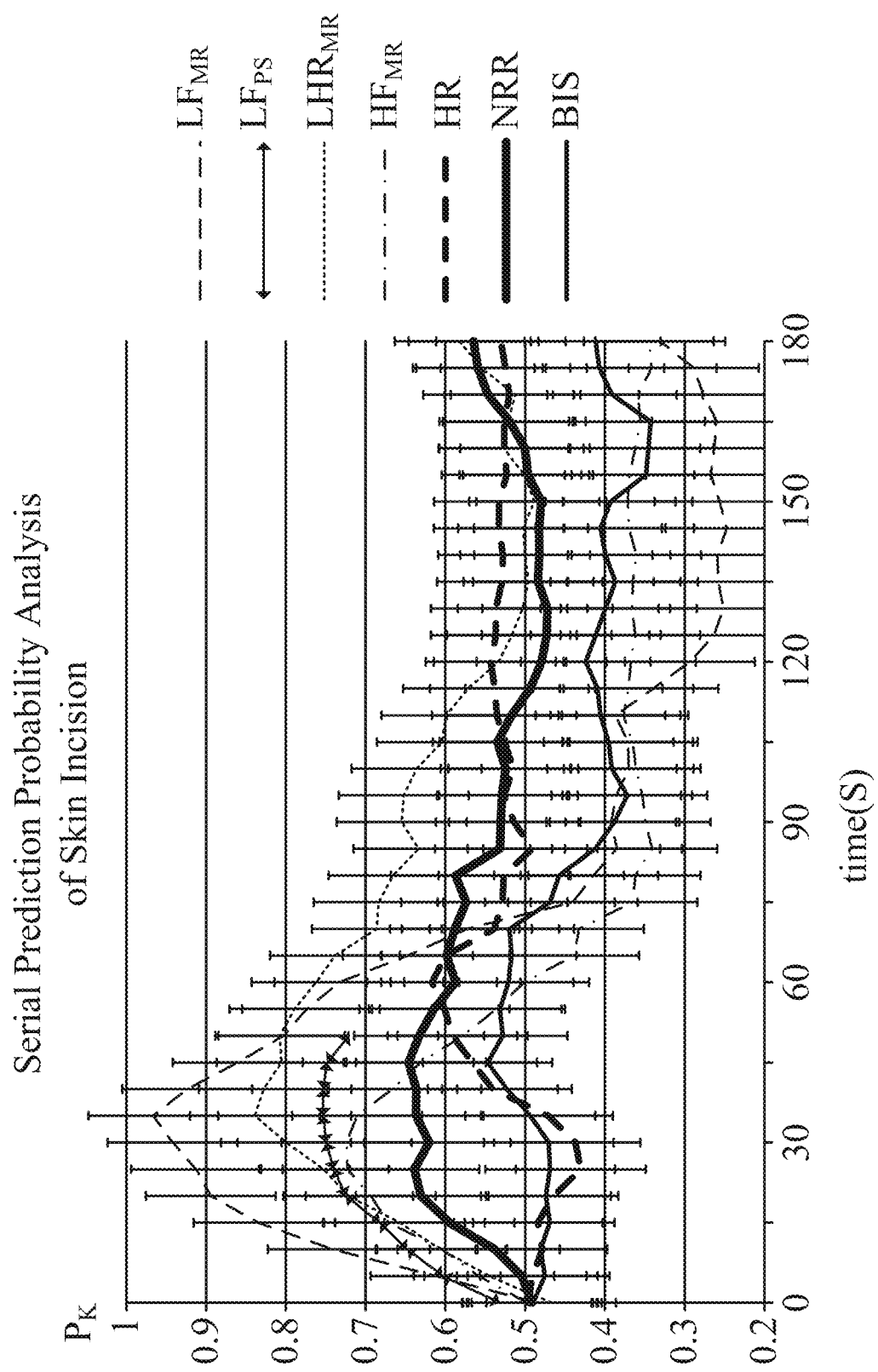
FIG. 15 is a serial Pk value to time graph illustrating the ability of each index predicting skin incision.
Figure 16:
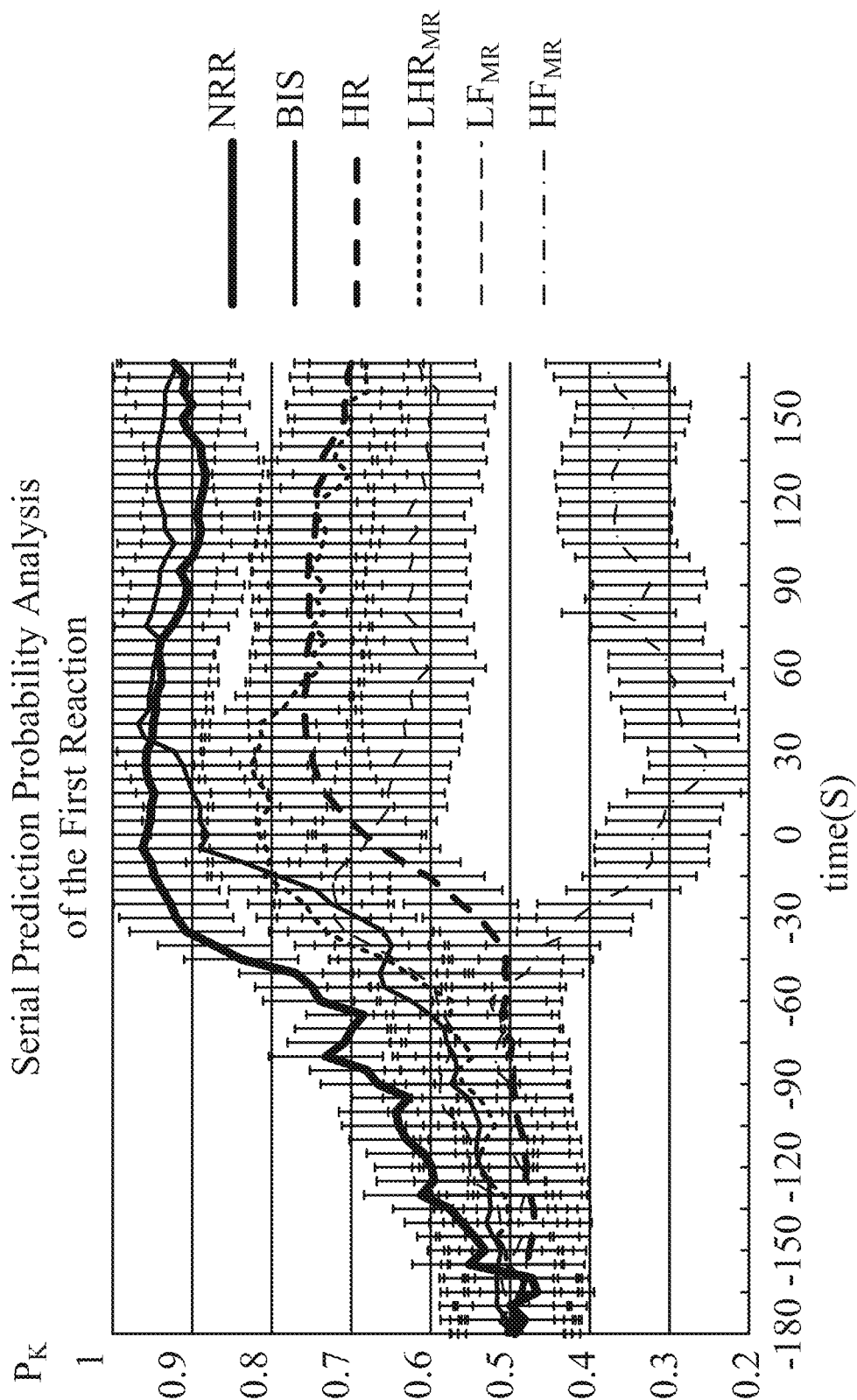
FIG. 16 is a serial Pk value to time graph illustrating the ability of each index predicting the first reaction.
Figure 17:
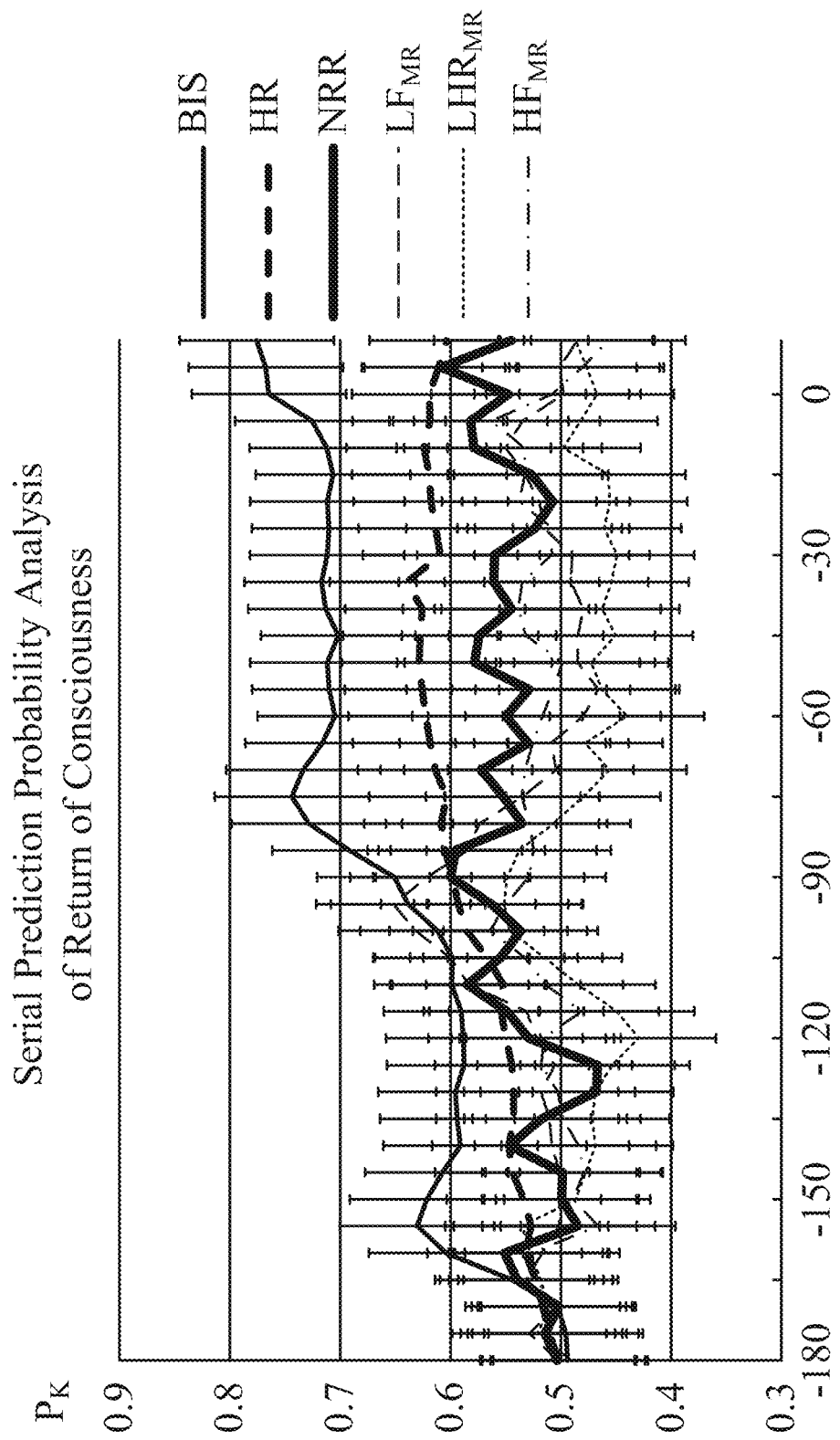
FIG. 17 is a serial Pk value to time graph illustrating the ability of each index predicting return of consciousness (ROC).

FIG. 14-FIG. 17 are Pk value to time graphs illustrating the abilities of each index predicting loss of consciousness (LOC), skin incision, the first reaction and return of consciousness (ROC). As shown in FIG. 14, BIS index predicts perfectly ($P_K$=1) 50 seconds after LOC. LOC is also associated with decrease in $LF_{MR}$, $HF_{MR}$, and HR. NRR does not predict LOC well. As shown in FIG. 15, in the serial PK analysis for skin incision, $LF_{MR}$ reaches maximum (PK>0.95) 30 seconds after skin incision. It predicts skin incision best, followed by $LHR_{MR}$ (PK<0.85). $LF_{MR}$ is also significantly better than BIS index ($P_K$<0.55) and NRR ($P_K$<0.65). $LF_{MR}$ is significantly better than $LF_{PS}$ ($P_K$<0.75). The above results demonstrate the technical advantage of MTFR spectrogram over the classical power spectrum. As shown in FIG. 16, in the serial $P_K$ analysis for the first reaction, NRR is ahead of BIS index (p<0.05 for 35 seconds). NRR effectively predicts the first reaction 30 seconds in advance ($P_K$>0.90). At the instance of the first reaction (0 seconds), both NRR and BIS index (both $P_K$ maxima>0.95) are significantly better than other parameters. The HRV indices and HR ($P_K$<0.83) are significantly worse than NRR. As shown in FIG. 17, BIS index predicts ROC best, and surpasses NRR, HR, and the HRV indices significantly. Representative values of indices in serial PK analyses are tabulated in table 3. Values are presented as median values, and the values in brackets are lower and upper quartiles respectively. $HF_{MR}$, $LF_{MR}$, and $LHR_{MR}$ are expressed in common logarithm (10 base) of milliseconds square. Heart rates are expressed in beats per minute. $T_0$ is 60 seconds before LOC; $T_1$ is 60 seconds after LOC; $T_2$ is 5 seconds before incision; T3 is 30 seconds after incision; T4 is 180 seconds before first reaction; T5 is 5 seconds after the first reaction; T6 is 180 seconds before ROC; T7 is 5 seconds after ROC.

frequency range in a frequency to power spectrum of RRI, and the fundamental rhythmic frequency is a frequency of a maximal power in a specific frequency range in a frequency to power spectrum of EDR (ECG-derived respiration).

|  | LOC | | skin incision | | first reaction | | ROC | |
|---|---|---|---|---|---|---|---|---|
|  | $T_0$ | $T_1$ | $T_2$ | $T_3$ | $T_4$ | $T_5$ | $T_6$ | $T_7$ |
| BIS | 97 | 54 | 39 | 41 | 61 | 73 | 80 | 86 |
|  | (94, 98) | (42, 68) | (36, 44) | (37, 44) | (70, 47) | (67, 80) | (77, 83) | (81, 94) |
| NRR | −0.26 | 0.09 | −0.14 | 0.04 | −0.80 | 0.47 | 0.36 | 0.43 |
|  | (−0.42, 0.21) | (−0.09, 0.31) | (−0.51, 0.02) | (−0.19, 0.21) | (−1.1, −0.38) | (0.29, 0.61) | (0.12, 0.51) | (0.19, 0.62) |
| $HF_{MR}$ | 2.37 | 1.50 | 1.21 | 1.42 | 1.44 | 1.07 | 1.11 | 1.25 |
|  | (2.05, 2.76) | (0.97, 1.66) | (0.94, 1.55) | (1.08, 1.81) | (1.09, 1.83) | (0.78, 1.23) | (0.91, 1.40) | (0.93, 1.60) |
| $LF_{MR}$ | 1.84 | 1.37 | 0.84 | 1.59 | 0.09 | 0.79 | 0.68 | 0.91 |
|  | (1.50, 2.27) | (1.01, 1.60) | (0.46, 0.94) | (1.25, 2.25) | (−0.37, 0.56) | (0.75, 1.31) | (0.01, 1.27) | (0.37, 1.26) |
| $LHR_{MR}$ | −0.42 | −0.03 | −0.50 | 0.24 | −1.33 | −0.25 | −0.44 | −0.34 |
|  | (−0.84, −0.27) | (−0.29, 0.19) | (0.46, 0.84) | (0.01, 0.50) | (−1.67, −0.66) | (−0.73, 0.06) | (−0.79, 0.10) | (−0.66, −0.12) |

According to the results above, it is found that NRR is able to predict the subject's first reaction effectively, rather than loss of consciousness (LOC) or return of consciousness (ROC). This may show that RSA regularity is associated with motor reactions, rather than an individual's consciousness. Since the cerebral cortex is primarily responsible for an individual's consciousness, while subcortical regions, such as the thalamus, of the brain are mainly responsible for motor reactions, NRR may reflect the subcortical regions. On the contrary, indices related to cortical EEC, such as BIS index, reflect activities of the cerebral cortex better, rather than the subcortical regions, resulting in better abilities to reflect ROC and LOC. The purpose of the experimental results described above is to demonstrate the clinical effectiveness and results when the method and apparatus for estimating depth of anesthesia in the invention are applied in clinical practice, and should not be regarded as limiting.

The present invention has been described with a preferred embodiment thereof and it is understood that various modifications, without departing from the spirit of the present invention, are in accordance with the embodiments of the present invention. Hence, the embodiments described are intended to cover the modifications within the scope and the spirit of the present invention, rather than to limit the present invention.

What is claimed is:

1. A method for estimating depth of anesthesia, comprising steps of:
   (a) acquiring an ECG signal;
   (b) quantifying regularity of respiratory sinus arrhythmia (RSA) to obtain an index based on the ECG signal; and
   (c) estimating depth of anesthesia based on the index;
   wherein the index obtained from quantifying the regularity is a ratio of a respiratory non-rhythmic component to a respiratory rhythmic component (NRR), the respiratory rhythmic component is a value representing extent of heart rate variability (HRV) affected by respiration, and the respiratory non-rhythmic component is a value representing extent of heart rate variability (HRV) not affected by respiration.

2. The method as claimed in claim 1, wherein the respiratory rhythmic component is the sum of RRI (R-R intervals) power in a specific bandwidth where a fundamental rhythmic frequency is located and RRI (R-R intervals) power in a specific bandwidth where a multiple of the fundamental rhythmic frequency is located in a specific 3. The method as claimed in claim 2, wherein the respiratory non-rhythmic component is total RRI power in a specific frequency range in the frequency to power spectrum of RRI minus the respiratory rhythmic component.

4. The method as claimed in claim 3, wherein the frequency to power spectrum of RRI and the frequency to power spectrum of EDR are an MTFR (multitaper time-frequency reassignment) spectrum of RRI and an MTFR spectrum of EDR respectively, and the respiratory non-rhythmic component, the respiratory rhythmic component, the fundamental rhythmic frequency, the multiple of the fundamental rhythmic frequency, the RRI power in a specific bandwidth where the fundamental rhythmic frequency is located, or the RRI power in a specific bandwidth where the multiple of the fundamental rhythmic frequency is located is derived from the MTFR spectrum of RRI and the MTFR spectrum of EDR.

5. The method as claimed in claim 4, wherein the fundamental rhythmic frequency is defined as the following formula:

$$f_r(t) = \underset{f \in R^+}{\operatorname{argmax}} MTFR_{EDR}(t, f),$$

and fr(t) is the fundamental rhythmic frequency.

6. The method as claimed in claim 4, wherein the respiratory rhythmic component is defined as the following formula:

$$P_r(t) = \sum_{n=1}^{k} \int_{n \cdot f_r - bHz}^{n \cdot f_r + bHz} MTFR_{RRI}(t, f) df \text{ for } k \cdot f_r < aHz,$$

Pr(t) is the respiratory rhythmic component, b is a bandwidth, k is a positive integer, and a is a maximum frequency used to define a specific frequency range.

7. The method as claimed in claim 6, wherein the ratio of the respiratory non-rhythmic component power to the respiratory rhythmic component power (NRR) is defined as the following formula:

$$NRR(t) = \log_{10}\left(\frac{HF_{MR}(t) - P_r(t)}{P_r(t)}\right),$$

NRR(t) is the ratio of the respiratory non-rhythmic component to the respiratory rhythmic component, and HFMR(t) is total RRI power in a specific frequency range in the MTFR spectrum of RRI.

8. An apparatus for estimating depth of anesthesia, comprising:
   an ECG signal acquiring unit acquiring an ECG signal in a non-invasive way, and outputting a digitized ECG signal; and
   an ECG signal analysis unit coupled with the ECG signal acquiring unit for receiving the digitized ECG signal, and quantifying regularity of respiratory sinus arrhythmia (RSA) to obtain an index based on the ECG signal for estimating depth of anesthesia;
   wherein the index obtained from quantifying the regularity is a ratio of a non-respiratory rhythmic component to a respiratory rhythmic component (NRR), the non-rhythmic component is a value representing the extent of HRV affected by respiration, and the non-rhythmic component is a value representing the extent of HRV not affected by respiration.

9. The apparatus as claimed in claim 8, wherein the respiratory rhythmic component is the sum of RRI (R-R intervals) power in a specific bandwidth where a fundamental rhythmic frequency is located and RRI (R-R intervals) power in a specific bandwidth where a multiple of the fundamental rhythmic frequency is located in a specific frequency range in a frequency to power spectrum of RRI, and the fundamental rhythmic frequency is a frequency of a maximal power in a specific frequency range in a frequency to power spectrum of EDR (ECG-derived respiration).

10. The apparatus as claimed in claim 9, wherein the respiratory non-rhythmic component is total RRI power in a specific frequency range in the frequency to power spectrum of RRI minus the respiratory rhythmic component.

11. The apparatus as claimed in claim 10, wherein the frequency to power spectrum of RRI and the frequency to power spectrum of EDR are an MTFR (multitaper time-frequency re-assignment) spectrum of RRI and a MTFR spectrum of EDR respectively, and the respiratory non-rhythmic component, the respiratory rhythmic component, the fundamental rhythmic frequency, the multiple of the fundamental rhythmic frequency, the RRI power in the fundamental rhythmic frequency, or the RRI power in a multiple of the fundamental rhythmic frequency are derived from the MTFR spectrum of RRI and the MTFR spectrum of EDR.

12. The apparatus as claimed in claim 11, wherein the fundamental rhythmic frequency is defined as the following formula:

$$f_r(t) = \underset{f \in R^+}{\mathrm{argmax}} MTFR_{EDR}(t, f),$$

and fr(t) is the fundamental rhythmic frequency.

13. The apparatus as claimed in claim 11, wherein the respiratory rhythmic component is defined as the following formula:

$$P_r(t) = \sum_{n=1}^{k} \int_{n \cdot f_r - bHz}^{n \cdot f_r + bHz} MTFR_{RRI}(t, f) df \text{ for } k \cdot f_r < aHz,$$

Pr(t) is the respiratory rhythmic component, b is a bandwidth, k is a positive integer, and a is a maximum frequency used to define a specific frequency range.

14. The apparatus as claimed in claim 13, wherein the ratio of the respiratory non-rhythmic component to the respiratory rhythmic component is defined as the following formula:

$$NRR(t) = \log_{10}\left(\frac{HF_{MR}(t) - P_r(t)}{P_r(t)}\right),$$

NRR(t) is the ratio of a respiratory non-rhythmic component to the respiratory rhythmic component, and HFMR(t) is the total RRI power in a specific frequency range in the frequency to power spectrum of RRI.

* * * * *